United States Patent [19]

McVay et al.

[11] 4,327,030
[45] Apr. 27, 1982

[54] PROCESS FOR REDUCING THE POLYUNSATURATES CONTENT IN MIXTURES OF UNSATURATED FATTY ACIDS AND/OR FATTY ACID ESTERS

[75] Inventors: Kenneth R. McVay, Fairfield; Stephen C. Lakes; Karl T. Zilch, both of Cincinnati, all of Ohio

[73] Assignee: Emery Industries, Inc., Cincinnati, Ohio

[21] Appl. No.: 234,280

[22] Filed: Feb. 13, 1981

[51] Int. Cl.$^3$ ............................................... C11C 3/00
[52] U.S. Cl. .................................... 260/407; 260/419; 260/420
[58] Field of Search ........................ 260/407, 419, 420

[56] References Cited

U.S. PATENT DOCUMENTS

| | | | |
|---|---|---|---|
| 2,479,857 | 8/1949 | Myers | 260/407 |
| 2,664,429 | 12/1953 | Goebel | 260/407 |
| 2,731,481 | 1/1956 | Harrison | 260/407 |
| 2,964,545 | 12/1960 | Harrison | 260/407 |
| 3,950,365 | 4/1976 | Singer et al. | 260/407 |

Primary Examiner—John F. Niebling
Attorney, Agent, or Firm—Kenneth D. Tremain

[57] ABSTRACT

A process for reducing the amount of polyunsaturated fatty acid and/or polyunsaturated fatty acid ester present in admixture with monounsaturated fatty acid and/or monounsaturated fatty acid ester is provided which comprises heating the admixture of fatty acids and/or fatty acid esters in the presence of a polymerization initiating amount of at least one organic peroxide at a temperature and for a period of time which is sufficient to effect the selective polymerization of a substantial amount of polyunsaturated fatty acid and/or polyunsaturated fatty acid ester present in said admixture, and thereafter separating the polymerized polyunsaturated fatty acid and/or polyunsaturated fatty acid ester from said admixture. The aforedescribed process is especially useful for reducing the amount of linoleic acid present in high oleic acid-content vegetable oils.

14 Claims, No Drawings

PROCESS FOR REDUCING THE POLYUNSATURATES CONTENT IN MIXTURES OF UNSATURATED FATTY ACIDS AND/OR FATTY ACID ESTERS

BACKGROUND OF THE INVENTION

1. Field of the Invention

This invention belongs to the field of fatty carboxylic acids and their esters and, more particularly, to the field of processes for reducing the polyunsaturates content of fatty acids and/or fatty acid esters.

2. Description of the Prior Art

Processes for preparing dimeric fatty acids are known. U.S. Pat. No. 2,731,481 to Harrison, et al. describes the dimerization of monounsaturated fatty acids, such as oleic acid, to provide dimeric acids which retain the unsaturation of the fatty acids from which they are prepared. To accomplish this, higher fatty acids or esters thereof having only one double bond in the fatty group are heated in an inert atmosphere to temperatures in excess of 50° C. in the presence of an organic peroxide catalyst of the formula $ROOR^1$, in which R is a tertiary alkyl group and $R^1$ is selected from the group consisting of tertiary alkyl and tertiary alkyl peroxyalkyl groups, e.g. di-tertiary butyl peroxide.

In accordance with the dimerization process described in U.S. Pat. No. 2,964,545, conjugated diunsaturated fatty acids or their lower alkyl esters, alone or in admixture with other fatty acids, either saturated or unsaturated, are converted to dimeric fatty acid under substantially the same conditions and in the presence of the same or similar organic peroxides disclosed in U.S. Pat. No. 2,731,481 to Harrison, et al., supra. Given the teachings of U.S. Pat. No. 2,731,481 to Harrison, et al. that monounsaturated fatty acids will undergo dimerization under essentially the same conditions which U.S. Pat. No. 2,964,545 to Harrison teaches will result in the dimerization of conjugated diunsaturated fatty acids, one skilled in the art would not consider the selective peroxide-initiated polymerization of diunsaturated fatty acids and/or fatty acid esters such as linoleic acid and/or methyl linoleate present in admixture with monounsatured fatty acids and/or fatty acid esters such as oleic acid and/or methyl oleate to be possible.

U.S. Pat. No. 3,950,365 to Singer, et al. describes a method for the purification of fatty acid mixtures, said to be especially useful for the production of oleic acid which is relatively free of linoleic acid, in which a fatty acid mixture is heated to 90°-150° C. in the presence of a particular type of organic microporous acid ion exchange resin resulting in selective dimerization/trimerization of the polyunsaturated fatty acid components of the mixture (e.g., linoleic acid) greatly increasing the boiling points of the polyunsaturates and facilitating their removal by distillation. There is no suggestion in this patent of selectively polymerizing polyunsaturated fatty acids in a fatty acid mixture employing a peroxygen compound. As noted above, one skilled in the art would have no reason to expect such a selective polymerization to be possible since the Harrison, et al. and Harrison patents show that both oleic acid and linoleic acid undergo dimerization when treated with peroxide.

SUMMARY OF THE INVENTION

It has now been very surprisingly discovered that under the conditions hereinafter stated, linoleic acid and/or other polyunsaturated fatty acids and fatty acid esters present in admixture with monounsaturated fatty acids and/or their esters can be selectively polymerizaed primarily to the dimer, and the polymerized polyunsaturates can thereafter be separated from the unaffected monounsaturated fatty acids/fatty acid esters employing known and conventional means such as fractional distillation in which case the polymerized polyunsaturates are recovered as a distillation residue.

Broadly stated, the present invention provides a process for reducing the amount of polyunsaturated fatty acid and/or polyunsaturated fatty acid ester present in admixture with monounsaturated fatty acid and/or monounsaturated fatty acid ester which comprises heating the admixture of fatty acids and/or fatty acid esters in the presence of a polymerization initiating amount of at least one organic peroxide polymerization initiator at a temperature and for a period of time which is sufficient to effect the selective polymerization of a substantial amount of polyunsaturated fatty acid and/or polyunsaturated fatty acid ester present in said admixture, and thereafter separating the polymerized polyunsaturated fatty acid and/or polyunsaturated fatty acid ester from said admixture.

Altogether contrary to what one skilled in the art would expect based upon the disclosure of U.S. Pat. No. 2,731,481 to Harrison, et al. supra, the dimerization process herein does not result in any significant dimerization of monounsaturated components but is substantially exclusively directed to the polyunsaturate converting the latter to a polymer, predominantly dimer, which can thereafter be separated by fractional distillation. Accordingly, the process of this invention provides a simple, rapid and economical procedure for separating polyunsaturated fatty acid materials from their monounsaturated analogs and is particularly applicable to the manufacture of food grade fatty acids from edible oils and fats where high heat stability is necessary or desired. Thus, for example, employing the process herein, fatty acids obtained from edible oils obtained from any of several vegetable sources such as palm oil, peanut oil, safflower oil, soybean oil, and the like, and typically containing from about 75 to about 85% by weight oleic acid, from about 15 to about 25% by weight linoleic acid and less than about 5% by weight percent saturated acids can undergo selective polymerization herein such that, following separation of the polymerizate, the resulting fatty acids will possess a linoleic acid content of less than about 5% by weight.

The term "polymerization" as used herein shall include the reactions of unsaturated fatty acids and fatty acid esters to provide dimers, trimers and other oligomers as well as the higher polymers of said fatty acids and fatty acid esters.

DESCRIPTION OF THE PREFERRED EMBODIMENTS

The admixtures of fatty acids and/or fatty acid esters which are useful starting materials herein are made up of fatty acids and/or monoesters of fatty acids prepared from lower monohydric aliphatic alcohols such as methanol, ethanol, propanol, isopropanol, n-butanol, s-butanol, t-butanol, and the like. In general, the useful fatty acid/ester admixtures possess from about 8 to about 26 carbon atoms in the fatty acid portion. The amount of polyunsaturated component(s) present in the starting admixtures can vary over fairly wide limits and advantageously is within the range of from about 3% to about 25% by weight of the total amount of fatty material. Typically, useful fatty acid/ester admixtures herein will contain from 0% to about 30% by weight of saturated component(s), from about 55% to 97% by weight of monounsaturated component(s) and from about 3% to 25% by weight, and preferably from about 5% to about 20% by weight, of polyunsaturated component(s). Where present, it is often preferable to pretreat the starting fatty acid/ester admixtures to remove the saturated component(s) therefrom. This can be readily and conveniently accomplished utilizing known and conventional solvent extraction procedures.

The organic peroxide polymerization initiators which are useful herein advantageously conform to the general formula $ROOR^1$ in which R is hydrogen or a hydrocarbon radical and $R^1$ is a hydrocarbon radical and preferably includes compounds having a tertiary alkyl peroxide radical. Included among such organic peroxides are di-tertbutyl peroxide which is preferred; 2,2-bis-t-butylperoxy propane; 2,2-bis-t-butylperoxy butane; 2,2-bis-t-butylperoxy pentane; 3,3-bis-t-butylperoxy pentane; t-butyl hydroperoxide; or cumene hydroperoxide.

The quantity of organic peroxide polymerization initiator can be widely varied and amounts of initiator of from about 0.5% to about 20%, and preferably from about 5% to about 15%, by weight of the fatty acid and/or fatty acid admixture are usually effective. It is within the scope of the invention to add the polymerization initiator all at once, continuously, or incrementally to the reaction medium.

The temperature which is employed depends upon the particular peroxide used and upon the reaction period desired. In general, temperatures should be in excess of 50° C. and preferably in the range of 100°–200° C.

The maximum temperature which can be employed is the decomposition temperature of the material being treated, and generally is in the neighborhood of 250° C. It is preferred, however, not to employ temperatures as high as 250° C. as these relatively high temperatures tend to promote an unacceptably high degree of peroxide decomposition.

Reaction pressures are not critical with both ambient and superatmospheric pressures being entirely satisfactory in most cases.

The reaction times for the process according to the present invention will be selected such as to achieve polymerization of at least a substantial amount of the polyunsaturates present in the starting material and generally can range from about 30 minutes to about 50 hours or more and more frequently, will range from about 2 to about 10 hours.

The process involves the mere admixture of the fatty acid/ester admixture with the organic peroxide polymerization initiator and the heating of the mixture, generally in an inert atmosphere, for the desired time and at the desired temperature. The peroxide is decomposed and consumed during the polymerization reaction and the decomposition products, primarily alcohols, can be removed from the reaction medium following completion of polymerization employing such known and conventional procedures as stripping at elevated temperature and reduced pressure. The mixture of products resulting from polymerization is separated, preferably by fractional distillation, into the unchanged monounsaturated and saturated fatty acids/esters as distillate and the polymerized polyunsaturated fatty acids/esters, made up largely of dimer products, as the distillation residue. The latter substances are also valuable products, especially in the area of synthetic resins and polyesters.

The following examples are further illustrative of the invention herein.

Free fatty acids derived from palm oil and safflower oil from which the stearic acid component was separated by solvent extraction (acetone) and the palmitic acid component was separated by fractional distillation were subjected, in sequence, to polymerization conditions (heating at ambient pressure and at reflux temperature for varying periods) employing di-tertbutyl peroxide (DTBP) as polymerization initiator and using fractional distillation for separation of the polymerized polyunsaturates. The conditions for the polymerizations and the analyses of the initial and final fatty acid mixtures are given in tabular form as follows:

| EXAMPLE | Wt. % DTBP | Reaction Time | Wt. % Initial Oleic Acid | Wt. % Initial Linoleic Acid | Wt. % Final Oleic Acid | Wt. % Final Linoleic Acid | Wt. % Reduction of Linoleic Acid** |
|---|---|---|---|---|---|---|---|
| 1 | 5 | 3 | 80.0 | 15.9 | 85.5 | 12.6 | 21 |
| 2 | 10 | 3 | 77.6 | 21.3 | 82.9* | 15.3 | 28 |
| 3 | 7 | 5 | 77.6 | 21.3 | 83.8 | 14.2 | 33 |
| 4 | 10 | 5 | 77.6 | 21.3 | 86.0 | 12.0 | 44 |
| 5 | 7 | 5 | 80.0 | 15.9 | 86.3 | 10.9 | 31 |
| 6 | 10 | 5 | 80.0 | 15.9 | 87.9 | 9.0 | 43 |
| 7 | 10 | 5 | 84.1 | 14.8 | 89.2 | 7.3 | 51 |
| 8 | 10 | 5 | 84.1 | 15.3 | 92.4 | 6.4 | 58 |
| 9 | 9 | 5 | 84.1 | 15.3 | 89.1 | 8.3 | 46 |

*98% cis- and 2% trans- content.
**Following separation by fractional distillation and recovery of polymerized linoleic acid as distillation residue.

As these data show, substantial reductions of the diunsaturated fatty acid, linoleic acid, were obtained herein without significantly affecting the monounsaturated fatty acid, oleic acid, with which the former was in admixture.

What is claimed is:

1. A process for reducing the amount of polyunsaturated fatty acid and/or polyunsaturated fatty acid ester present in admixture with monounsaturated fatty acid and/or monounsaturated fatty acid ester which comprises heating the admixture of fatty acids and/or fatty acid esters in the presence of a polymerization initiating amount of at least one organic peroxide polymerization initiator at a temperature and for a period of time which is sufficient to effect the selective polymerization of a substantial amount of polyunsaturated fatty acid and/or polyunsaturated fatty acid ester present in said admixture, and thereafter separating the polymerized polyunsaturated fatty acid and/or polyunsaturated fatty acid ester from said admixture.

2. The process of claim 1 wherein the fatty acids and/or fatty acid ester contain from about 8 to about 26 carbon atoms.

3. The process of claim 2 wherein the admixture of fatty acids and/or fatty acid esters, prior to heating, contains from about 3% to about 25% by weight of polyunsaturated component.

4. The process of claim 2 wherein the admixture of fatty acids and/or fatty acid esters contains from about 15% to about 25% by weight of linoleic acid and/or linoleic acid ester and from about 75% to about 85% by weight of oleic acid and/or oleic acid ester.

5. The process of claim 1 wherein the organic peroxide polymerization initiator conforms to the general formula ROOR$^1$ in which R is hydrogen or a hydrocarbon radical and R$^1$ is a hydrocarbon radical.

6. The process of claim 5 wherein the organic peroxide polymerization initiator possesses a tertiary-alkyl peroxy radical.

7. The process of claim 5 wherein the organic peroxide polymerization initiator is di-tertbutyl peroxide; 2,2-bis-t-butylperoxy propane; 2,2-bis-t-butylperoxy butane; 2,2-bis-t-butylperoxy pentane; 3,3-bis-t-butylperoxy pentane; t-butyl hydroperoxide; or cumene hydroperoxide.

8. The process of claim 1 wherein the amount of organic peroxide polymerization initiator employed is from 0.5 to about 20% by weight of the admixture of fatty acids and/or fatty acid esters.

9. The process of claim 1 wherein the amount of organic peroxide polymerization initiator employed is from about 5% to about 15% by weight of the admixture of fatty acids and/or fatty acid esters.

10. The process of claim 1 wherein heating is carried out to a temperature of from about 50° C. to about 250° C.

11. The process of claim 1 wherein heating is carried out to a temperature of from about 100° C. to about 200° C.

12. The process of claim 1 wherein heating is conducted for from about 30 minutes to about 50 hours.

13. The process of claim 1 wherein the polymerized fatty acid and/or polymerized fatty acid ester is separated from admixture with monounsaturated fatty acid and/or monounsaturated fatty acid ester by fractional distillation.

14. A process for reducing the amount of linoleic acid present in admixture with oleic acid which comprises heating the admixture of acids in the presence of from about 5% to about 15% by weight of an organic peroxide of the general formula ROOR$^1$ in which R is hydrogen or a hydrocarbon radical and R$^1$ is a hydrocarbon radical to a temperature of from about 100° C. to about 200° C. for from about 30 minutes to about 50 hours to selectively polymerize the linoleic acid, and thereafter separating the polymerized linoleic acid from the oleic acid by fractional distillation.

* * * * *